US012751737B2

(12) United States Patent
Seckin

(10) Patent No.: US 12,751,737 B2
(45) Date of Patent: Oct. 6, 2026

(54) METHOD FOR SURGICAL TREATMENT OF OVARY

(71) Applicant: Tamer Ahmet Seckin, New York, NY (US)

(72) Inventor: Tamer Ahmet Seckin, New York, NY (US)

( * ) Notice: Subject to any disclaimer, the term of this patent is extended or adjusted under 35 U.S.C. 154(b) by 751 days.

(21) Appl. No.: 18/152,788

(22) Filed: Jan. 11, 2023

(65) Prior Publication Data

US 2024/0225694 A1 Jul. 11, 2024

(51) Int. Cl.
*A61B 17/42* (2006.01)

(52) U.S. Cl.
CPC .................................... *A61B 17/42* (2013.01)

(58) Field of Classification Search
CPC ...................................................... A61B 17/42
See application file for complete search history.

(56) References Cited

U.S. PATENT DOCUMENTS

2020/0289574 A1* 9/2020 Brown .................... A61P 15/08
2021/0260151 A1* 8/2021 Seckin ................. A61K 31/167

OTHER PUBLICATIONS

Ancel Blaustein, Anatomy and Histology of the Human Ovary, 1977, A. Blaustein (ed.), Pathology of the Female Genital Tract Â © Springer Science+Business Media, New York, Chapter 19, pp. 365-386 (Year: 1977).*

Valerio Di Nicola, Omentum a powerful biological source in regenerative surgery, 2019, Regenerative Therapy, vol. 11, pp. 182-191 (Year: 2019).*

G. Shoshany, R. Shofty, E. Livne, L. Hayari, and D. Mordechovitz, Testicular Neovascularization by 'Omentotesticulopexy': A Possible Adjuvant in the Surgical Correction of High Undescended Testes, 1996, Journal of Pediatric Surgery, vol. 31, No. 9, pp. 1229-1232 (Year: 1996).*

* cited by examiner

*Primary Examiner* — David W Berke-Schlessel
*Assistant Examiner* — Trent R Clarke

(57) ABSTRACT

Present invention provides a method for surgical treatment of an ovary, wherein an incision is formed in an external wall of the ovary such that a supply path extends from the incision into the ovary, and wherein an insert is provided and a distal portion of the insert is inserted through the incision, such that a proximal portion of the insert is arranged outside of the ovary to supply the ovary externally.

6 Claims, 5 Drawing Sheets

METHOD FOR SURGICAL TREATMENT OF OVARY

FIELD OF INVENTION

Present invention relates to a surgical method for treatment of ovary.

BACKGROUND OF INVENTION

Known techniques for surgical treatment of premature ovarian insufficiency or failure include ovarian wedge resection and ovarian drilling. Ovarian drilling and ovarian wedge resection are treatment options to reduce the amount of androgen producing tissue in women with polycystic ovarian syndrome (PCOS), which is the primary cause of anovulation, which results in female infertility. Ovarian drilling and ovarian wedge resection involves tissue destruction and removal. Both techniques may cause adhesions complicating postoperative outcomes. Ovarian cortex tissue transplant has also been performed to treat infertility.

Ovaries comprise a dual blood supply. A main blood supply is from the ovarian artery and a second source of arterial blood comes from a collateral uterine artery. Diseases in ovary often affect the blood supply of ovary.

An improved surgical stimulation technique of ovary is needed without the drawbacks of known techniques.

BRIEF DESCRIPTION OF THE PRESENT INVENTION

Present invention provides a method for surgical treatment of an ovary of a female, providing a slit in the ovary by slitting the ovary, providing a longitudinal insert having a distal portion and a proximal portion at an opposite side of and connecting to the distal portion, inserting the distal portion into the slit such that the proximal portion of the insert is arranged outside of the ovary to supply the distal portion and to feed the ovary externally via the distal portion. The distal portion and the proximal portion may be integral with the insert. Slitting may comprise incising the ovary longitudinally substantially from end to end and at least into a virtual central longitudinal axis of the ovary; and inserting the distal portion comprises inserting the distal portion through the incision such that the proximal portion of the insert is arranged outside of the ovary to supply the distal portion and to feed the ovary externally via the distal portion.

Compared to injection treatment, the present invention is more effective by supplying the ovary from a larger reservoir during a longer time and over a larger surface area of the flat slit.

Incising the ovary comprises forming an incision opening in an external wall of the ovary such that a supply path extends from the incision opening into the ovary, and wherein the distal portion of the insert is inserted through the incision opening. The insert may have a substantially wedge shaped flat body, the distal portion comprising a narrower width than the proximal portion.

Incising the ovary may comprise incising the ovary lengthwise substantially along major axis thereof, such that the ovary is partially slit by a longitudinal incision having a substantially longitudinal shape. The insert may be inserted transversally along the longitudinal incision and the distal end is thereby sandwiched by the ovary in a substantially lengthwise direction of the ovary. The method comprises thereby stretching the incision to fit the insert through the incision into the ovary. The insert is placed within the incision lengthwise and has a longitudinal axis substantially parallel to the incision.

Incising the ovary may comprise incising a surface of the ovary that is exposed to the peritoneal cavity, substantially facing the space surrounded by the ovaries or facing the other ovary or facing away from the mesovarium. Incising the ovary may comprise incising a free surface including one or more of posterior or medial surface of the ovary.

Incising the ovary may comprise incising a surface of the ovary that is exposed to the peritoneal cavity between the superior (vascular) pole attached to the suspensory ligament of the ovary and the inferior (uterine) pole attached to the ovarian ligament. Incising the ovary may comprise incising the ovary lengthwise on a virtual line substantially extending the ovarian ligament forming a longitudinal incision.

The method may further comprise incising the other ovary as described above.

The inventive method further comprises closing the incision opening. Closing may comprise suturing, clipping or stapling at least partially such that the distal portion of the insert is arranged within the incision, and the proximal portion of the insert is arranged outside of the ovary after closing the incision and that the distal portion gets pressed between the slit ovary parts.

Closing the incision opening may comprise suspending the insert at the ovary and fixing the insert to the ovary at the incision, such that the proximal portion of the insert is arranged outside of the ovary and the distal portion of the insert is arranged inside the ovary after closing the incision.

The insert may comprise omental tissue and the method may comprise surgically extending the omentum by omental transposition, inserting the omentum through the incision to vascularize the ovary, placing the omentum within the ovary partially and suturing the omentum to the ovary. Extending the omentum by omental transposition may comprise preparing a vascularized omental pedicle flap, such that the omental pedicle flap has continuous vascular supply, wherein the omental pedicle flap is still connected to the omentum after being partially placed in the ovary. The method may further comprise folding a distal portion of the omental pedicle flap along an edge thereof by rolling into a roll such that to form the distal portion of the insert. The vascularized omental pedicle flap may be prepared by mobilization of the omentum from stomach or transverse colon. The method may comprise inserting the roll of omental pedicle flap through the longitudinal incision opening transversally such that the roll is placed at least partially within the ovary having a longitudinal axis of folding being substantially parallel to the longitudinal incision. The method may comprise suspending and fixing the roll of omental pedicle flap at the ovary when closing the longitudinal incision opening together with the roll of omental pedicle flap. The roll may have a substantially cylindrical or conical shape, wherein a free end of the roll substantially faces the ovarian ligament and an opposite end of the roll is integral with the omental pedicle flap.

The method may further comprise arranging the proximal portion of the insert or a proximal and possibly not folded portion of omental pedicle flap connected to the roll substantially in the peritoneal cavity. The method may further comprise providing a space in the peritoneal cavity surrounded by the ovaries, uterus and colon and arranging the proximal portion or the proximal portion of the omental pedicle flap substantially in the surrounded space. The method may comprise displacing the ovaries to surround the space by the ovaries, uterus and colon.

The insert may comprise an implant and the method may comprise placing the implant into the incision, preferably wherein the implant comprises a hollow structure. The hollow structure may comprise a flexible body to get rolled and to fit partly into the incision.

The implant may comprise a chamber containing a preparation to feed the preparation through the implant into the supply path and the ovary. The method may comprise to arrange the chamber at least partially outside of the ovary when closing the incision. The preparation may comprise Platelet-rich plasma (PRP) and/or Methylene Blue (MB). The chamber may comprise a flexible wall or a piston to enable a change of volume of the chamber. The chamber may be biased to inject the preparation into the supply path. The chamber may contain a pressurized fluid or a spring biased piston. The method may comprise to pressurize the chamber by filling with air. The body of the chamber is made of a membrane having a permeable portion or output ports at least in the distal portion to release the PRP and MB out of the implant. The implant may comprise a puncturable attachment portion for suturing or stapling. The puncturable attachment portion may comprise a puncturable tab that may be sutured or stapled to the ovary. The method may comprise suturing or stapling the puncturable attachment portion to the ovary by suturing or stapling the slit ovary parts together with the roll of omental pedicle flap. The method may comprise to puncture the chamber when closing the incision thereby forming output ports.

The method may further comprise applying MB onto the distal portion of the insert or the incision.

The method may further comprise providing a sleeve and applying the sleeve to enclose the ovary at least partially to fix the insert in place. The sleeve may comprise a web or mesh like structure.

The method may comprise contacting an outer surface of the insert with an inner incision surface of the ovary for continuous area-wide stimulation of the ovary. The method may comprise continuously feeding the ovary over the insert. Continuously feeding the ovary may comprise continuously feeding the ovary along a longitudinal portion of the insert, wherein the longitudinal portion of the insert comprises permeability features. The method may comprise continuously feeding the insert. Continuously feeding the insert may comprise continuously feeding the insert along a longitudinal portion of the insert, wherein the insert comprises continuous vascular supply, or wherein the insert comprises continuous pressurized supply from the chamber.

Other advantages of the present invention are defined in the appended claims.

BRIEF DESCRIPTION OF THE DRAWINGS

The above-described and other objects and features of the present invention will become more apparent from the following detailed description of preferred embodiments of the invention and the accompanying drawings.

DETAILED DESCRIPTION OF PREFERRED EMBODIMENTS

The preferred embodiments of the present invention will be described below with reference to accompanying figures.

Figure 1A:
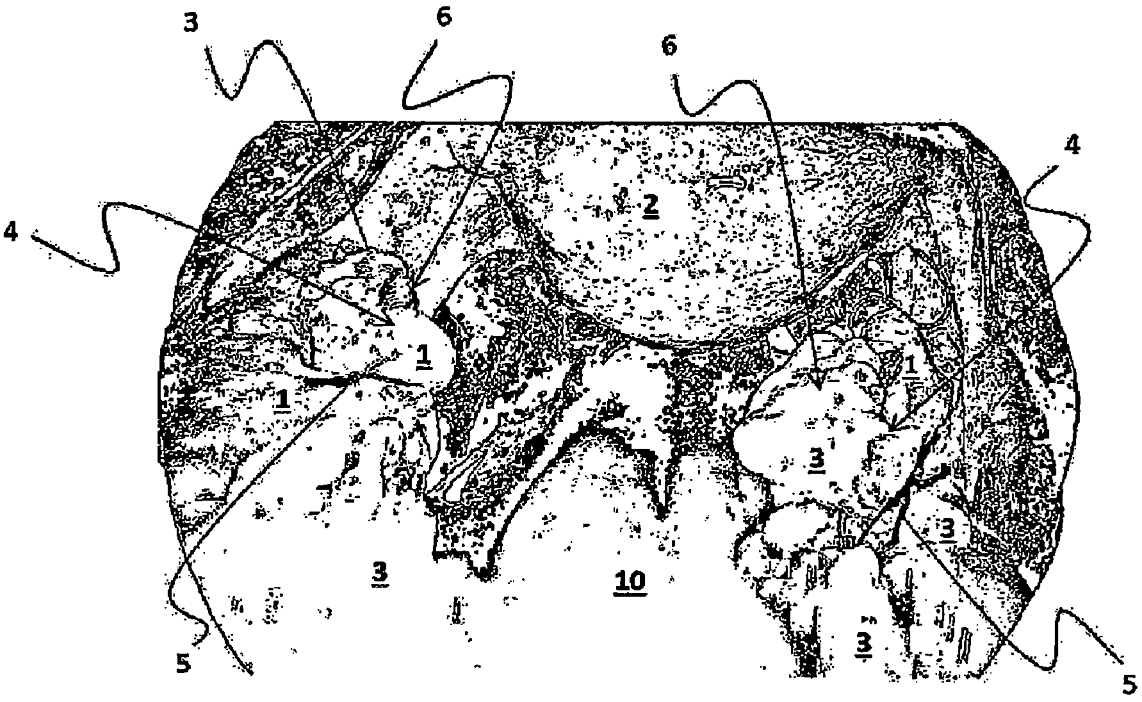
FIG. 1*a* is a picture of a laparoscopic surgery site including ovaries of a female patient, showing implementation of the method according to the present invention.
Figure 1B:
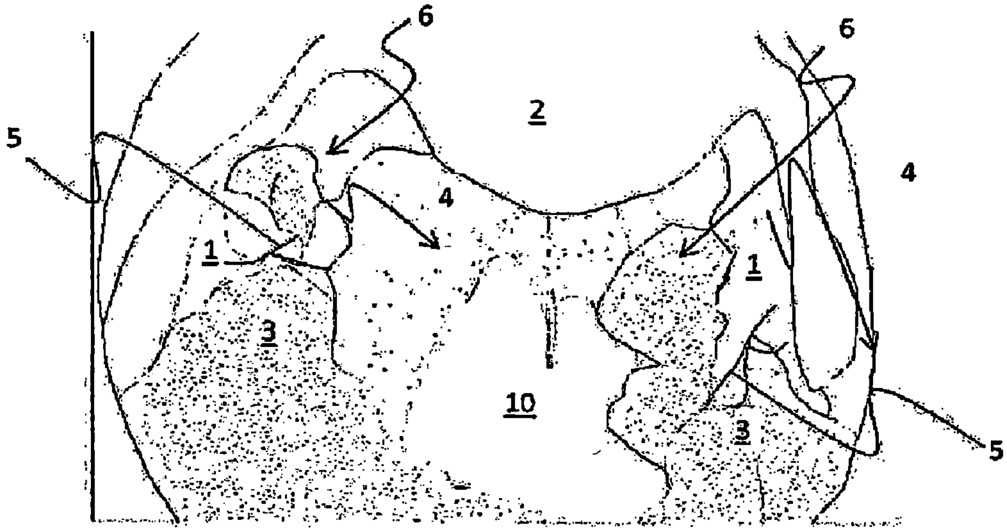
FIG. 1*b* illustrates schematically a representation of the surgery site of FIG. 1*a;*

FIG. 1*a* shows a preferred embodiment including an implementation of the method for treatment of ovaries of a female patient according to the present invention during a laparoscopic surgery. FIG. 1*b* illustrates schematically a representation of the surgery site of FIG. 1*a*. FIGS. 1*a* and 1*b* show ovaries (1), uterus (2) and vascularized omental pedicle flaps (3). The ovaries (1) are incised lengthwise along their major axes and are thereby partially slit by respective longitudinal incisions (4). Longitudinal openings are formed in the external walls of the ovaries (1) by the incisions (4). The omental pedicle flaps (3) are prepared by mobilization of the omentum from stomach or transverse colon, wherein the omentum is surgically extended by omental transposition, and wherein end portions of the omental pedicle flaps (3) are folded along respective edges into rolls. The rolls form inserts (6) that are partially inserted into respective ovaries (2) via the longitudinal incisions (4) transversally. The method comprises thereby stretching the incisions (4) to fit the inserts (6) through the incisions (4) into the respective ovaries (1). Proximal portions of the omental pedicle flaps (3) connected to respective rolls are still integral with the omentum after the rolls being inserted through the incisions (4), such that the omental pedicle flaps (3) have continuous vascular supply. The inserts (6) in form of rolls of omental pedicle flaps (3) are fixed and suspended at the ovaries (1) by sutures (5) that are applied when suturing the slit ovary parts together. Methylene blue is applied to the omental pedicle flaps (3) and outer surfaces of the rolls and to the incision surfaces.

The rolls are sandwiched in the respective longitudinal incisions (4) between the slit ovary parts in a substantially lengthwise direction of each ovary (1). The rolls have substantially conical shapes, wherein free ends of the rolls substantially face the ovarian ligament and opposite ends of the rolls are integral with the omental pedicle flap.

The preferred embodiment comprises arranging the omental pedicle flaps (3) substantially in the peritoneal cavity. The method further comprises surrounding a space in the peritoneal cavity by the ovaries (1), uterus (2) and colon (10) and arranging the omental pedicle flaps (3) substantially in the surrounded space. The method comprises displacing the ovaries (1) to surround the space by the ovaries (1), uterus (2) and colon (10). The method further comprises forming the incision (4) in a free surface including one or more of posterior and medial surface of the ovary (1) exposed to the peritoneal cavity, substantially facing the space surrounded by the ovary (1) or facing the other ovary (1) or facing away from the mesovarium. The method further comprises forming the incision (4) in the free surface including one or more of posterior or medial surface of the ovary (1) between the superior pole attached to the suspensory ligament of the ovary (1) and the inferior pole attached to the ovarian ligament and on a virtual line substantially extending the ovarian ligament. The method further comprises forming a further incision (4) in a further free surface including one or more of posterior surface of the other ovary (1) in a similar way.

Figure 2:
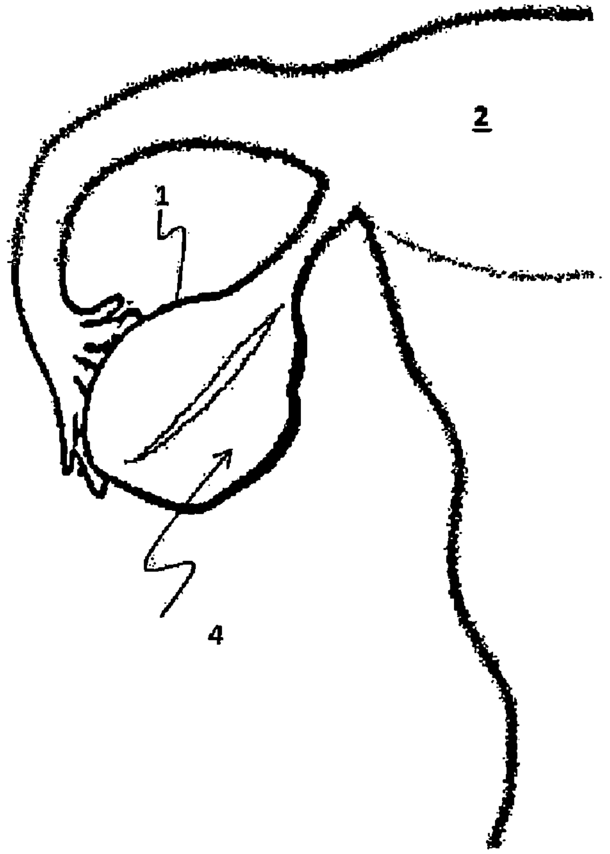
FIG. 2 illustrates schematically a representation of a surgery site including an ovary of a female patient.
Figure 3A:
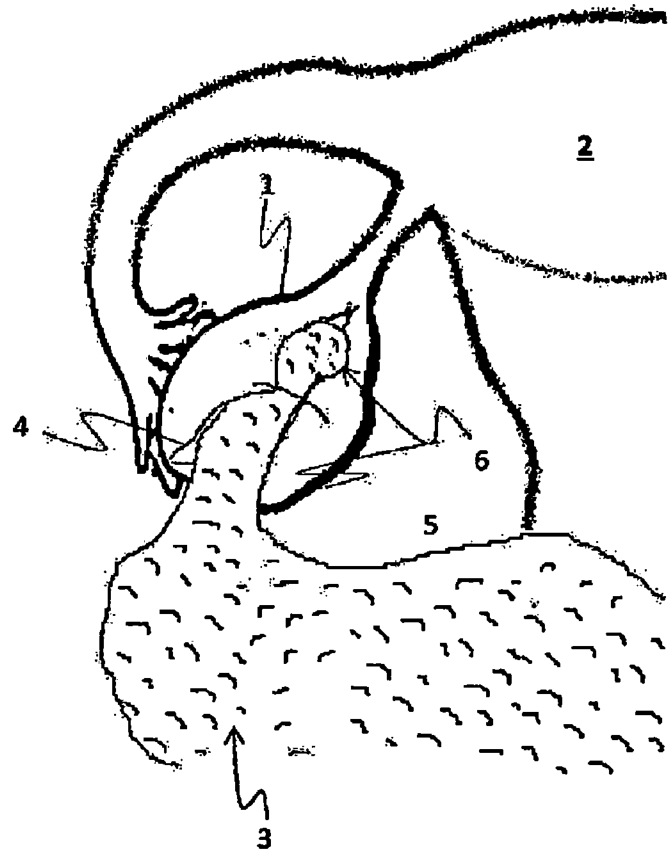
FIG. 3*a* illustrates schematically a representation of implementation of the method according to the present invention.
Figure 3B:
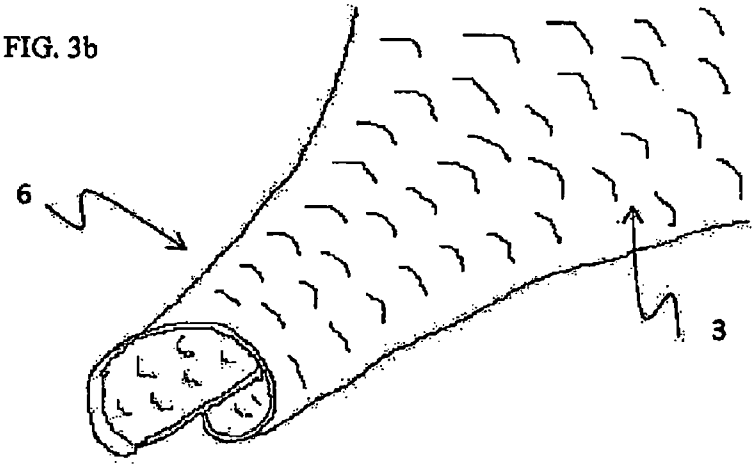
FIG. 3*b* illustrates schematically a detailed representation of an end portion of an insert shown in FIG. 3*a;*

FIG. 2 illustrates an ovary partially slit lengthwise by a longitudinal incision (4). FIG. 3*a* illustrates schematically a representation of implementation of the method for treatment of ovary according to the present invention, wherein an omental pedicle flap (3) is prepared by mobilization of the omentum from stomach or transverse colon, wherein the omentum is surgically extended by omental transposition. FIG. 3*b* illustrates schematically a representation of a distal portion of the omental pedicle flap (3), which is folded into a roll, forming an insert (6) that is partially inserted into the ovary (2) via the incision (4). A distal portion of the insert (6) is inside the ovary (1), whereas a proximal portion of the insert (6) is outside of the ovary (1), wherein the distal portion and the proximal portion are connected along the longitudinal incision (4). The omental pedicle flap (3) is still connected to the omentum via the proximal portion after being inserted through the incision (4) and partially placed within the ovary (4), such that the omental pedicle flap (3) has continuous vascular supply via the proximal portion along the longitudinal incision (4). The insert (6) in form of roll of omental pedicle flap (3) is fixed in the ovary by a suture (5) that is applied when suturing the slit ovary parts together. An outer surface of the insert (6) contacts the inner incision surface of the ovary (1) for a continuous area-wide stimulation of the ovary. The insert (6) has continuous vascular supply along a longitudinal portion of the insert (6).

Figure 4:
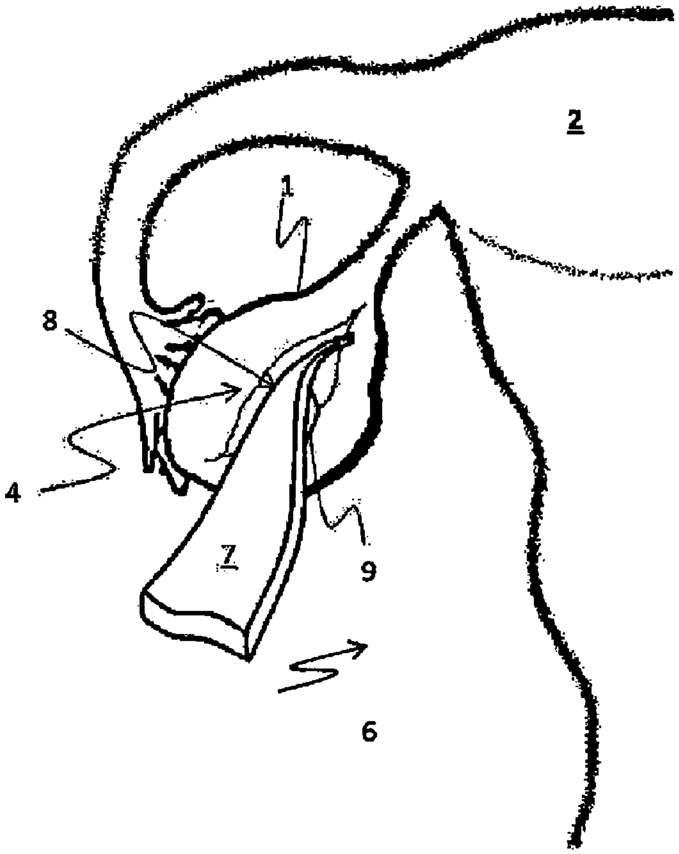
FIG. 4 illustrates schematically a representation of an alternative implementation of the method according to the present invention.
Figure 5:
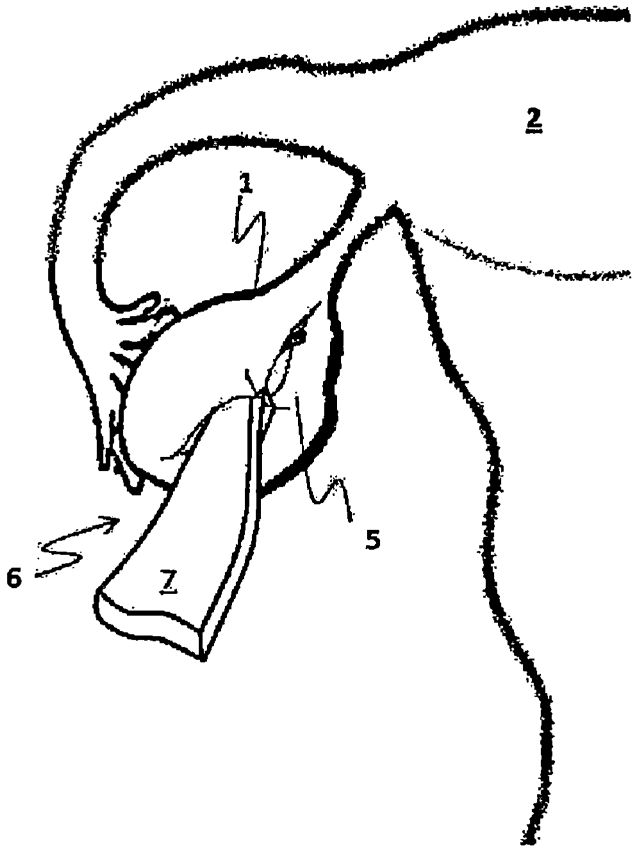
FIG. 5 illustrates schematically a further representation of the alternative implementation of FIG. 4.

FIGS. 4 and 5 show an alternative implementation of the method for treatment of ovary according to the present invention, wherein an insert (6) made of an implant is partially inserted into the ovary (1) through the incision (4). A distal portion (8) of the implant is placed within the ovary (1) during the inventive method. The implant comprises a flexible body defining a chamber (7) containing Platelet-rich plasma (PRP) and Methylene Blue (MB). PRP is prepared during the implementation of the method for treatment of ovary from a blood sample of the patient and filled into the chamber (7). At least a part of the chamber (7) is arranged substantially outside of the ovary (1) during the inventive method and comprises a flexible wall to enable a change of volume of the chamber (7). The chamber (7) is biased to continuously inject the PRP and MB into the ovary (1). The chamber (7) is filled with air and pressurized by the flexible wall to bias the PRP and MB from the chamber (7) into the ovary (1). The body of the chamber (7) is made of a membrane having a permeable portion or output ports at least in the distal portion to release the PRP and MB out of the implant. The implant comprises a puncturable tab (9) that is sutured to the ovary (1) via the suture (5) closing the incision (4). The chamber (7) is punctured when closing the incision thereby forming output ports to release PRP and MB. An outer surface of the distal portion of the insert (6) contacts the inner incision surface of the ovary (1) for a continuous area-wide stimulation of the ovary (1). The distal portion (8) of the insert (6) has continuous pressurised supply. The distal portion (8) and the proximal portion are integral parts of the insert (6). The implant is a pad-like structure having a substantially wedge shaped flat body, the distal portion comprising a narrower width than the proximal portion.

Many other examples or adaptations of the above embodiments will be apparent to those skilled in the art upon review of the above description without departing from the scope of the invention. The preferred embodiment of the invention has been described above in the drawings and description of the preferred embodiments. While these disclosures directly describe the above embodiments, it is understood that those skilled in the art may contemplate modifications and/or variations to the particular embodiments shown and described herein. Each of the following claims is incorporated herein as a separate preferred embodiment. Certain features of the disclosed embodiments may have been shown exaggerated in scale or in somewhat schematic form and some details of conventional elements may not have been shown in the interest of clarity and conciseness. The word "one (a, an)" in this specification appropriately means "one or more" or "at least one".

The invention claimed is:

1. A method for surgical treatment of ovary, comprising:
- providing a slit in the ovary by slitting the ovary,
- providing a longitudinal insert having a first portion and a second portion,
- folding the first portion of an omental pedicle flap along an edge thereof by rolling into a roll such that to form the first portion of the insert,
- inserting the first portion into the slit,
- arranging the second portion outside of the ovary,
- closing the slit by suturing such that the insert is suspended at the ovary and the first portion is arranged inside the ovary and supplied via the second portion to feed the ovary externally;
- wherein providing the insert comprises providing the insert comprising an implant having a biased chamber containing a preparation.

2. The method according to claim 1, wherein feeding the ovary comprises continuously supplying the ovary with platelet-rich plasma and/or methylene blue via the first portion from the second portion, wherein the second portion comprises the biased chamber having a flexible wall, wherein the chamber comprises platelet-rich plasma and/or methylene blue.

3. The method according to claim 1, wherein providing the insert comprises providing the insert having continuous vascular supply or continuous pressurized supply; and
- closing the slit comprises suturing the slit.

4. The method according to claim 1, further comprising pressurizing the chamber.

5. A method for surgical treatment of ovary, comprising:
- providing a slit in the ovary by slitting the ovary,
- providing a longitudinal insert having a first portion and a second portion,
- inserting the first portion into the slit,
- arranging the second portion outside of the ovary,
- closing the slit by suturing such that the insert is suspended at the ovary and the first portion is arranged inside the ovary and supplied via the second portion to feed the ovary externally,
- wherein providing the insert comprises providing the insert comprising an implant having a chamber containing a preparation.

6. The method according to claim 5, further comprising pressurizing the chamber.

* * * * *